(12) United States Patent
Ricci

(10) Patent No.: US 7,875,002 B2
(45) Date of Patent: Jan. 25, 2011

(54) STENT DELIVERY SYSTEM AND METHOD OF USE

(76) Inventor: Donald R. Ricci, 4443 West 3rd Avenue, Vancouver, BC (CA) V6R 1M9

(*) Notice: Subject to any disclaimer, the term of this patent is extended or adjusted under 35 U.S.C. 154(b) by 0 days.

(21) Appl. No.: 12/467,549

(22) Filed: May 18, 2009

(65) Prior Publication Data

US 2009/0287146 A1 Nov. 19, 2009

Related U.S. Application Data

(63) Continuation of application No. 10/671,716, filed on Sep. 29, 2003, now abandoned, which is a continuation of application No. 09/501,981, filed on Feb. 11, 2000, now abandoned.

(51) Int. Cl.
*A61M 29/00* (2006.01)

(52) U.S. Cl. .............. 604/96.01; 604/164.05; 604/264; 623/1.11; 606/108

(58) Field of Classification Search ............. 604/96.01, 604/103.01, 103.04, 103.05, 102.01, 102.02, 604/915; 606/108, 192, 194, 195, 199; 623/1.11
See application file for complete search history.

(56) References Cited

U.S. PATENT DOCUMENTS

| | | | |
|---|---|---|---|
| 4,748,982 A | 6/1988 | Horzewski et al. | |
| 5,161,534 A * | 11/1992 | Berthiaume | 600/434 |
| 5,195,978 A | 3/1993 | Schiffer | |
| 5,205,822 A | 4/1993 | Johnson et al. | |
| 5,290,232 A | 3/1994 | Johnson et al. | |
| 5,334,187 A | 8/1994 | Fischell et al. | |
| 5,458,613 A * | 10/1995 | Gharibadeh et al. | 606/194 |
| 5,460,185 A * | 10/1995 | Johnson et al. | 600/585 |
| 5,554,118 A | 9/1996 | Jang | |
| 5,569,296 A | 10/1996 | Marin et al. | |
| 5,685,847 A | 11/1997 | Barry | |
| 5,792,144 A | 8/1998 | Fischell et al. | |
| 5,833,706 A | 11/1998 | St. Germain et al. | |
| 5,840,008 A * | 11/1998 | Klein et al. | 600/3 |
| 6,007,517 A | 12/1999 | Anderson | |
| 6,007,522 A * | 12/1999 | Agro et al. | 604/264 |
| 6,083,232 A * | 7/2000 | Cox | 606/128 |
| 6,106,487 A * | 8/2000 | Duane et al. | 600/585 |
| 6,190,358 B1 * | 2/2001 | Fitzmaurice et al. | 604/103.04 |
| 6,849,077 B2 * | 2/2005 | Ricci | 606/108 |
| 6,869,416 B2 * | 3/2005 | Windheuser et al. | 604/164.05 |
| 2004/0193142 A1 * | 9/2004 | Agro et al. | 604/528 |
| 2009/0270905 A1 * | 10/2009 | Ricci | 606/192 |

* cited by examiner

*Primary Examiner*—Nicholas D Lucchesi
*Assistant Examiner*—Quynh-Nhu H Vu
(74) *Attorney, Agent, or Firm*—Katten Muchin Rosenman LLP

(57) ABSTRACT

A balloon dilation catheter comprising: a tubular member having a proximal end and a distal end and an inflatable balloon disposed at the distal end of the tubular member. The tubular member comprises a first lumen disposed in communication with an interior of the inflatable balloon and a second lumen for receiving a guidewire substantially along the entire length of the tubular member. The second lumen has a first opening at the proximal end of the tubular member and a second opening at the distal end of the tubular member. A first slit is disposed longitudinally from the first opening along substantially the entire length of the tubular member to permit separation of the guidewire with respect to the second lumen. The subject balloon dilation catheter provides improved rapid exchange advantages of either the catheter or the guidewire used in a catheterization technique.

21 Claims, 6 Drawing Sheets

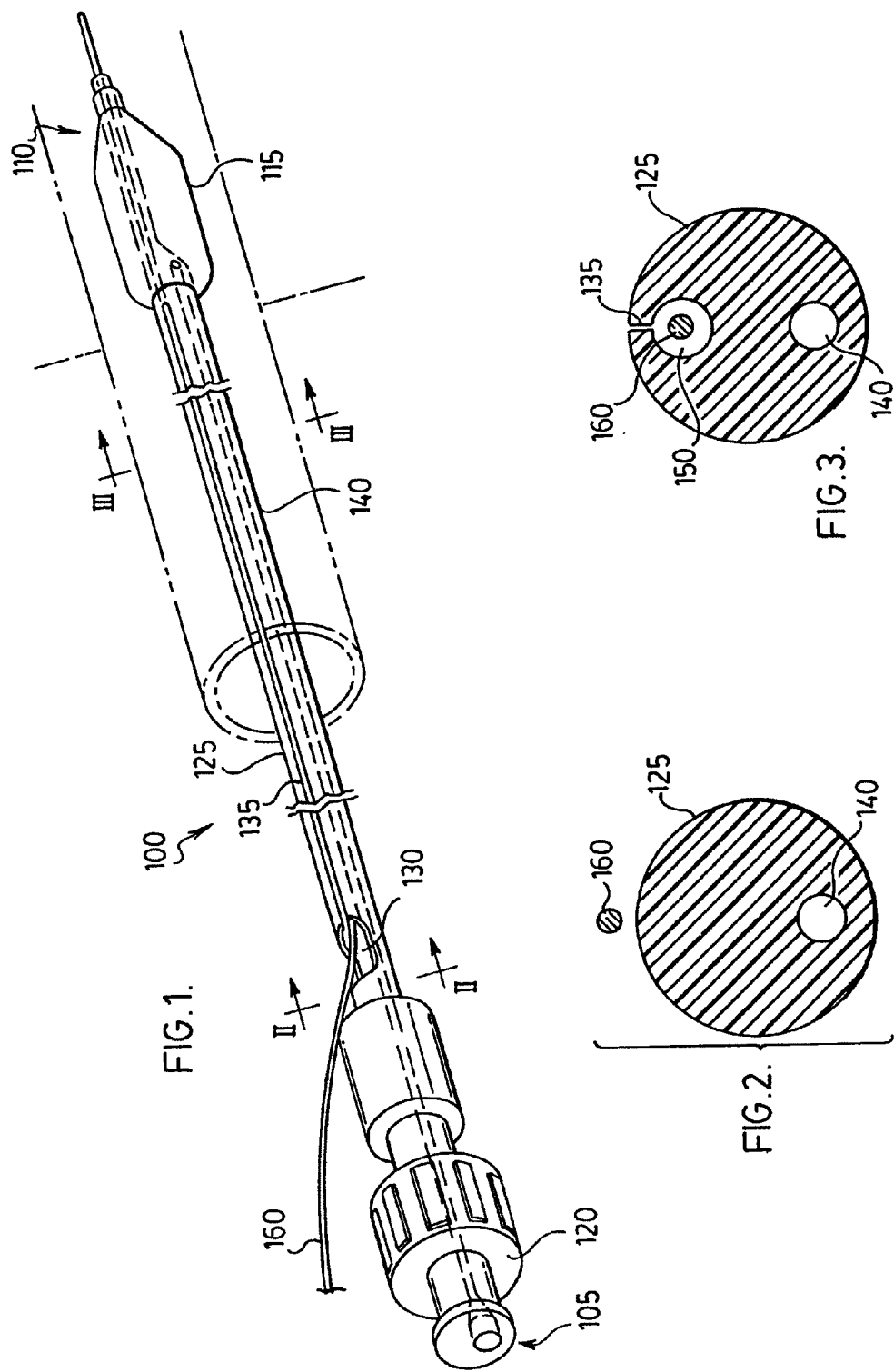

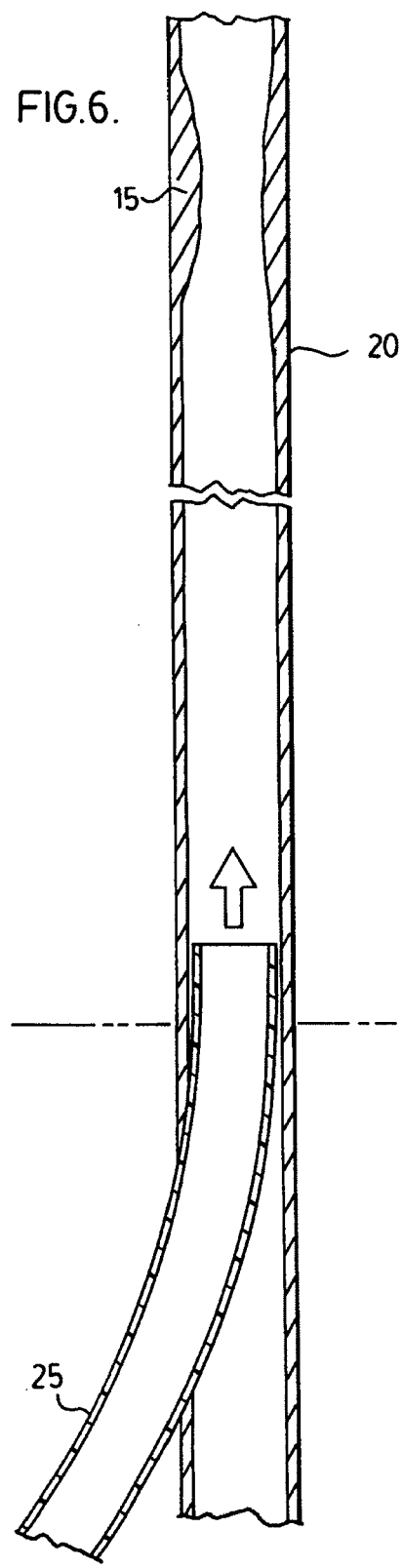
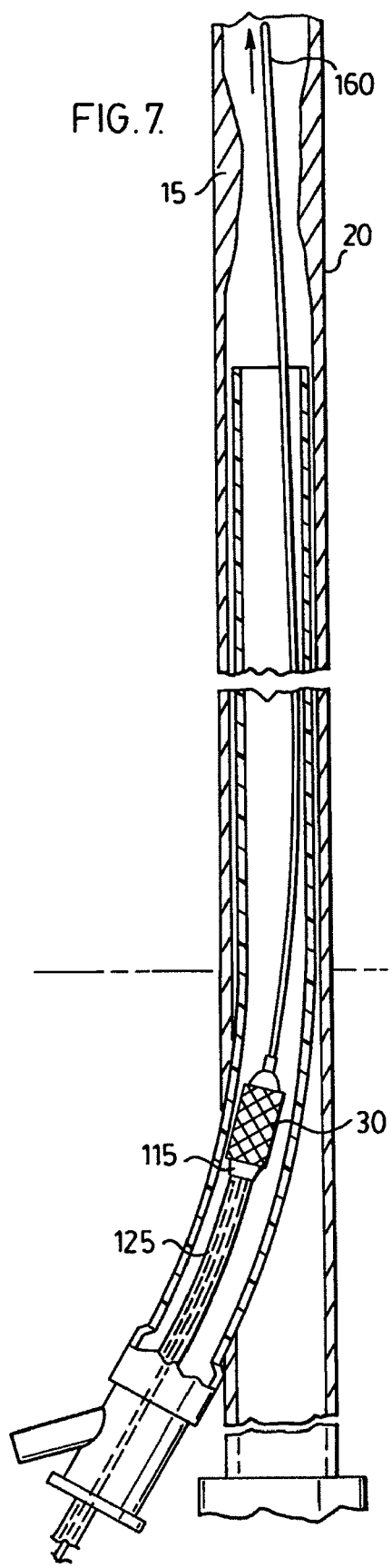

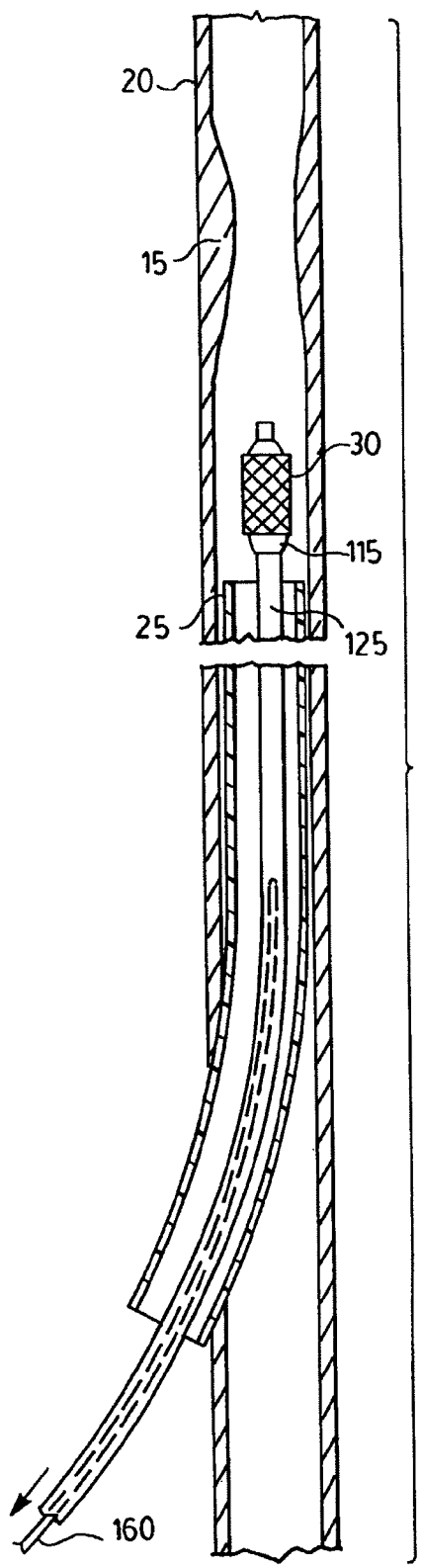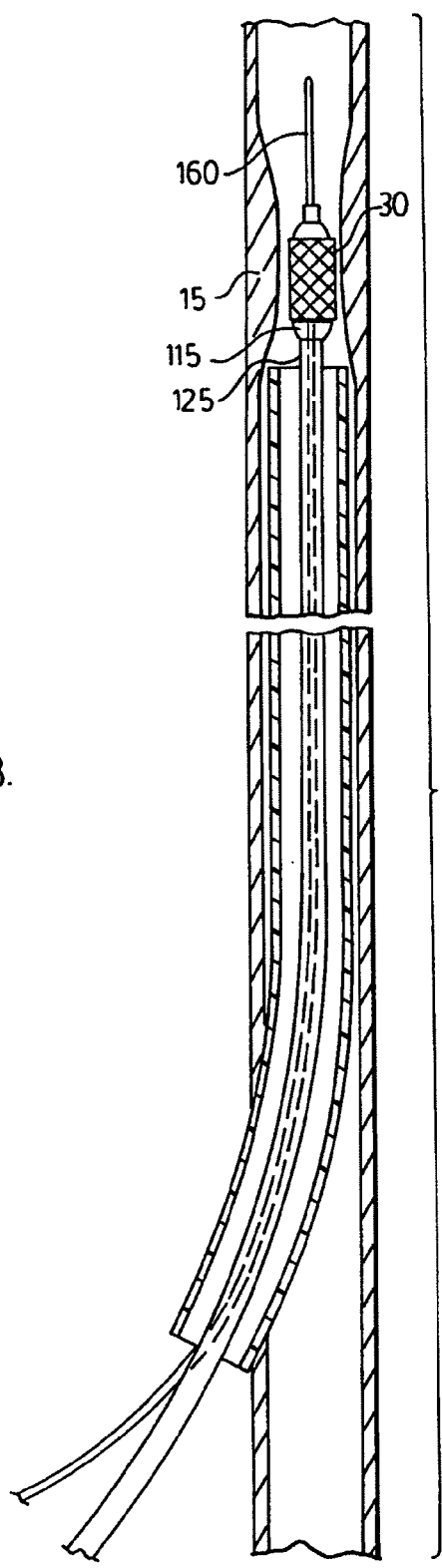

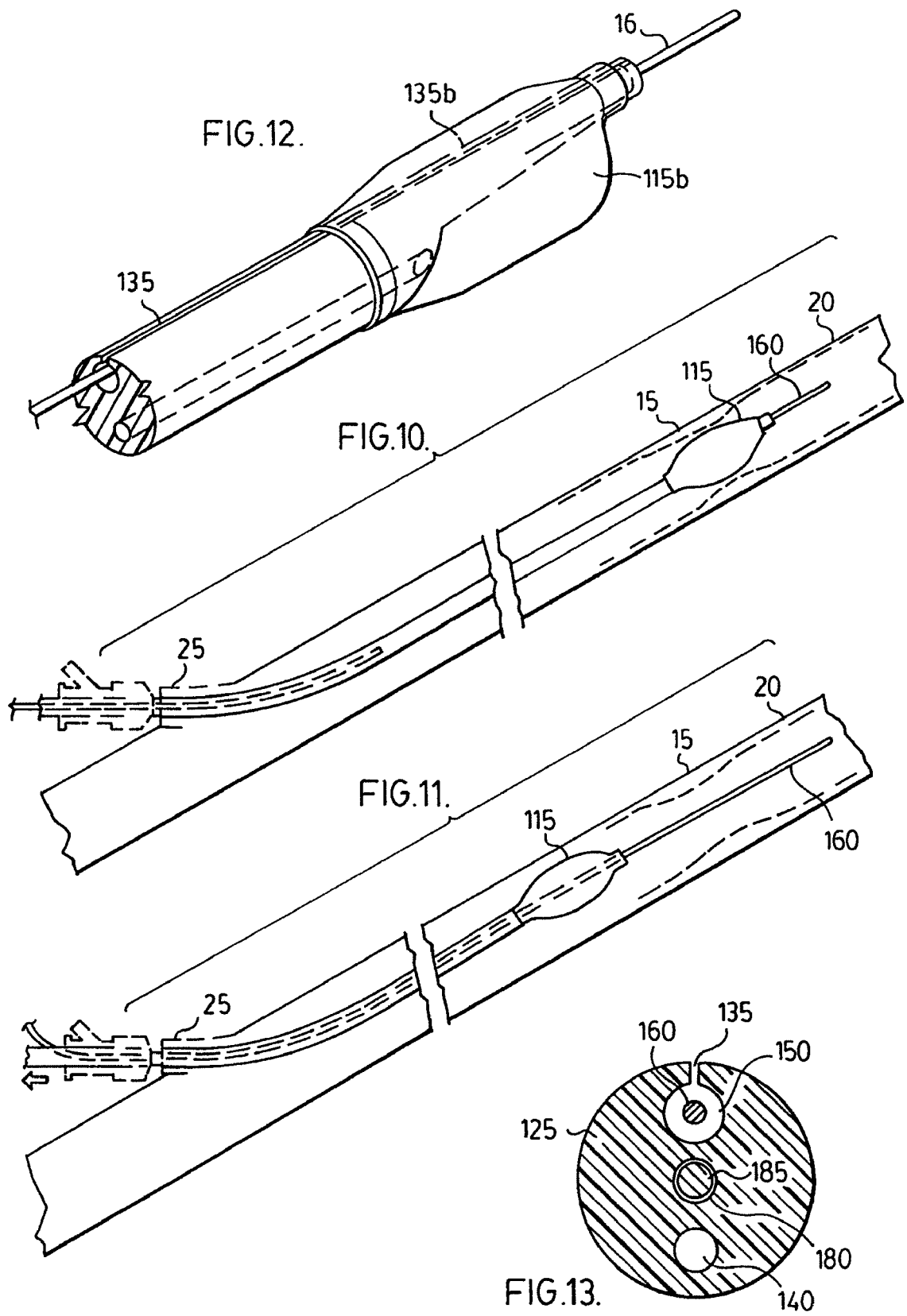

STENT DELIVERY SYSTEM AND METHOD OF USE

This application is a continuation of U.S. patent application Ser. No. 10/671,716, filed Sep. 29, 2003, which is a continuation of Ser. No. 09/501,981, filed Feb. 11, 2000, now abandoned, the contents of both incorporated herein by reference.

BACKGROUND OF THE INVENTION

1. Field of the Invention

In one of its aspects, the present invention relates to a balloon dilation catheter. In another of its aspects, the present invention relates to a catheterization method.

2. Brief Description of the Prior Art

Balloon dilation catheters have been known for many years. Originally, such catheters were used in interventional techniques such as angioplasty.

In recent years, balloon dilation catheters have also been used to facilitate endovascular prosthesis' such as stents. Stents are generally known. Indeed, the term "stent" has been used interchangeably with terms such as "intraluminal vascular graft" and "expansible prosthesis". As used throughout this specification, the term "stent" is intended to have a broad meaning and encompasses any expandable prosthetic device for implantation in a body passageway (e.g., a lumen or artery).

In the past dozen years, the use of stents has attracted an increasing amount of attention due to the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire structure of the stent so that the latter is urged in place against the body passageway. As indicated above, the amount of force applied is at least that necessary to expand the stent (i.e., the applied force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

See, for example, any of the following patents:
U.S. Pat. No. 4,323,071 (Simpson et al.),
U.S. Pat. No. 4,411,055 (Simpson et al.),
U.S. Pat. No. 4,616,648 (Simpson),
U.S. Pat. No. 4,661,094 (Simpson),
U.S. Pat. No. 4,733,665 (Palmaz),
U.S. Pat. No. 4,739,762 (Palmaz),
U.S. Pat. No. 4,800,882 (Gianturco),
U.S. Pat. No. 4,907,336 (Gianturco),
U.S. Pat. No. 5,035,706 (Gianturco et al.),
U.S. Pat. No. 5,037,392 (Hillstead),
U.S. Pat. No. 5,041,126 (Gianturco),
U.S. Pat. No. 5,092,873 (Simpson et al.),
U.S. Pat. No. 5,102,417 (Palmaz),
U.S. Pat. No. 5,147,385 (Beck et al.),
U.S. Pat. No. 5,269,793 (Simpson),
U.S. Pat. No. 5,282,824 (Gianturco),
U.S. Pat. No. 5,316,023 (Palmaz et al.),
U.S. Pat. No. 5,415,634 (Glynn et al.),
U.S. Pat. No. 5,462,529 (Simpson et al.),
U.S. Pat. No. 5,755,771 (Penn et al.),
U.S. Pat. No. 5,980,570 (Simpson),
International patent application PCT/CA97/00151 (Penn et al.), and
International patent application PCT/CA97/00152 (Penn et al.), for a discussion on previous stent designs and deployment systems.

Given the development of stent design, the prior art has also focussed on delivery systems for stent deployment.

One particular delivery system is taught by U.S. Pat. No. 4,748,982 [Horzewski et al. (Horzewski)]. Horzewski teaches a reinforced balloon dilation catheter with a slitted exchange sleeve. Essentially, the catheter comprises a tubular member having a first lumen and a second lumen. A dilation balloon is mounted on the distal end of the tubular member and is in communication with the first lumen. An opening (or notch) is disposed in the tubular member intermediate its proximal and distal ends for receiving a guidewire which travels through the second lumen and emanates out of the distal end of the tubular member. A slit is disposed on the longitudinal portion of the tubular member between the opening and an area 0.5-1 cm proximal the dilation balloon. Thus, as illustrated in FIG. 1 of Horzewski, the guidewire travels partly within a lumen in the catheter (approximately 10-15 cm) and partly along the outside of the catheter (approximately 80-90 cm). This approach is also known as a "monorail" delivery system. The principal advantage of this approach is that it permits so-called "rapid exchange" of the balloon catheter with another balloon catheter. In design, the exchange is facilitated by the provision of the above-mentioned slit so that the actual exchange is done over the balloon portion only (approximately 3 cm). The principal disadvantages of this approach include: less than optimum steerability of the guidewire, difficulties in moving the guidewire with respect to the catheter, less than optimum torque control and inability to exchange the guidewire while leaving the catheter in place. The catheter illustrated by Horzewski has not gained widespread commercial popularity.

Another approach for catheterization is the so-called "over the wire" approach—this approach is discussed in many of the above-mentioned U.S. patents naming John P. Simpson as an inventor. In this approach, the catheter comprises a tubular member having a first lumen and a second lumen. A dilation balloon is mounted on the distal end of the tubular member and is in communication with the first lumen. The second lumen runs through the length of the tubular member. An opening is disposed in the tubular member at its proximal end for receiving a guidewire which travels through second lumen and emanates out of the distal end of the tubular member. Thus, in the "over the wire" approach, the guidewire is enpassed by the second lumen along the entire length of the tubular member (approximately 90-105 cm). The principal advantages of the this approach include: optimum steerability, smoother movement of the guidewire with respect to the catheter (due to the coaxial relationship thereof), optimum torque control and the ability to exchange the guidewire while leaving the catheter in place. The principal is disadvantage of this approach is that exchange with another balloon catheter is relatively cumbersome (i.e., compared to the "monorail" approach discussed above.

Accordingly, it would be desirable to have a balloon dilation catheter which combined the advantages of the abovementioned "monorail" approach and "over the wire" approach while obviating or mitigating the disadvantages of these approaches. It would be further advantageous if the balloon dilation catheter were readily adaptable to be used in various interventional techniques such as endovascular prosthesis delivery, angioplasty and the like.

SUMMARY OF THE INVENTION

It is an object of the present invention to provide a novel balloon dilation catheter.

It is another object of the present invention to provide a novel catheterization method.

Accordingly, in one of its aspects, the present invention provides a balloon dilation catheter comprising:
a tubular member having a proximal end and a distal end;
an inflatable balloon disposed at the distal end of the tubular member;
a first lumen disposed in the tubular member and in communication with an interior of the inflatable balloon;
a second lumen disposed in the tubular member for receiving a guidewire substantially along its entire length, the second lumen having a first opening at the proximal end of the tubular member and a second opening at the distal end of the tubular member; and
a first slit disposed longitudinally from the first opening along substantially the entire length of the tubular member to permit separation of the guidewire with respect to the second lumen.

In another of its aspects, the present invention provides a catheterization kit comprising:
a guide catheter;
a guide wire; and
a balloon dilation catheter comprising: a tubular member having a proximal end and a distal end; an inflatable balloon disposed at the distal end of the tubular member;
a first lumen disposed in the tubular member and in communication with an interior of the inflatable balloon; a second lumen disposed in the tubular member for receiving the guidewire substantially along its entire length, the second lumen having a first opening at the proximal end of the tubular member and a second opening at the distal end of the tubular member; and a first slit disposed longitudinally from the first opening along substantially the entire length of the tubular member to permit separation of the guidewire with respect to the second lumen.

In yet another of its aspects, the present invention provides a stent-mounted balloon catheter comprising:
a tubular member having a proximal end and a distal end;
an inflatable balloon disposed at the distal end of the tubular member;
a stent mounted on the inflatable balloon;
a first lumen disposed in the tubular member and in communication with an interior of the inflatable balloon;
a second lumen disposed in the tubular member for receiving a guidewire substantially along its entire length, the second lumen having a first opening at the proximal end of the tubular member and a second opening at the distal end of the tubular member; and
a first slit disposed longitudinally from the first opening along substantially the entire length of the tubular member to permit separation of the guidewire with respect to the second lumen.

Thus, the present inventors have discovered a balloon catheter which combines the advantages of the "over the wire" approach (i.e., optimum steerability, smoother movement of the guidewire with respect to the catheter (due to the coaxial relationship thereof), optimum torque control and the ability to exchange the guidewire while leaving the catheter in place) with the principal advantage of the "monorail" approach (i.e., rapid exchange of the balloon catheter with another balloon catheter while leaving the guidewire in place).

As used throughout this specification, the term "tubular member", when used in the context of the present balloon dilation catheter is intended to mean a portion of the catheter generally tubular in construction and generally representing the large majority of the overall length of the balloon dilation catheter. Typically, the tubular member will be at least about 75%, more preferably at least about 85%, most preferably at least about 95%, of the overall length of the balloon dilation catheter.

BRIEF DESCRIPTION OF THE DRAWINGS

Embodiments of the present invention will be described with reference to the accompanying drawings wherein like numerals designate like parts and in which:

FIG. 1 illustrates a perspective view of an embodiment of the present balloon dilation catheter;

FIG. 2 is a sectional view along line II-II in FIG. 1;

FIG. 3 is a sectional view along line III-III in FIG. 1;

FIGS. 5-11 illustrate steps in various catheterization techniques employing the present balloon dilation catheter;

FIG. 12 illustrates a modified balloon for use in the present balloon dilation catheter; and FIG. 13 illustrates a preferred embodiment of a modified tubular member for use in the present balloon dilation catheter.

DETAILED DESCRIPTION OF THE PREFERRED EMBODIMENTS

Figure 4:
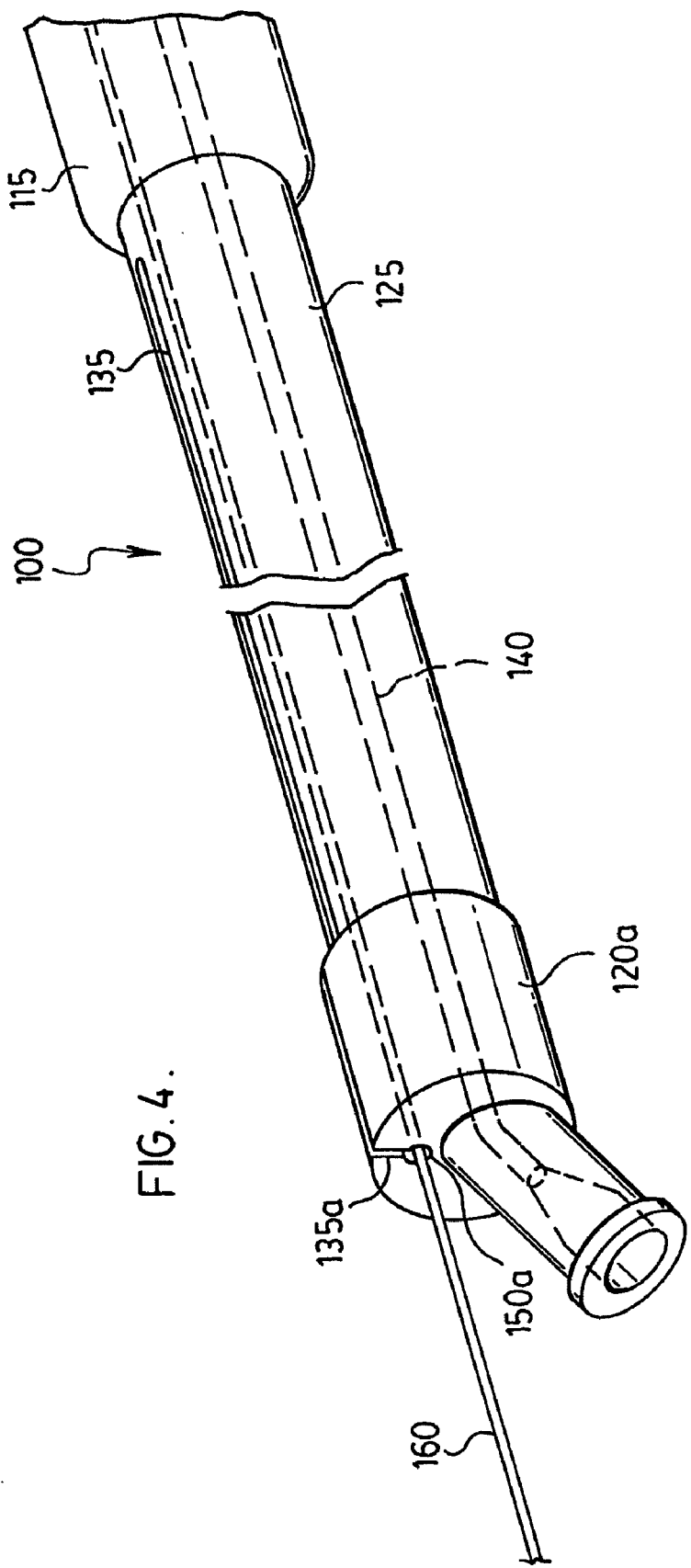
FIG. 4 illustrates an exploded view of modified proximal end of the balloon dilation catheter illustrated in FIG. 1.

Thus, with reference to FIGS. 1-3, there is illustrated a balloon dilation catheter 100. Balloon dilation catheter 100 comprises a proximal end 105 and a distal end 110. Distal end 110 of balloon dilation catheter 100 comprises an expandable balloon 115. Proximal end 105 of balloon dilation catheter 100 comprises an single lumen Luer-type adaptor 120. Disposed between adaptor 120 and balloon 115 is a tubular member 125.

As will be apparent from FIG. 1, disposed in tubular member 125 is an opening 130. Also disposed in tubular member 125 is a slit 135 which extends from opening 130 to a point in tubular member 125 just proximal balloon 115.

With particular reference to FIGS. 2 and 3, tubular member 125 comprises a first lumen 140 and a second lumen 150. First lumen 140 is designed to be in communication with an interior of balloon 115. The design of the interface between balloon 115 and first lumen 140 is conventional—see for example Horzewski referred to hereinabove. The construction of tubular member 125 having opening 130, slit 135, first lumen 140 and second lumen 150 is conventional—see Horzewski referred to hereinabove.

With further reference to FIGS. 1-3, it will be apparent that opening 130 is designed to receive a guidewire 160. Guidewire 160 passes through second lumen 150 and out of a distal opening of tubular member 125 beyond balloon 115.

In FIG. 4, there is illustrated a modification of balloon dilation catheter 100 illustrated in FIGS. 1-3.

Specifically, in FIG. 4, Luer-type adaptor 120a is modified to contain a lumen 150a in communication with a slit 135a. As will be apparent to those of skill in the art, lumen 150a is in communication with second lumen 150 in tubular member 125. Further, slit 135a is in communication with slit 135 in tubular member 125. The modification of balloon dilation catheter 100 illustrated in FIG. 4 eliminates the need for having opening 130 disposed in tubular member 125 illustrated in FIG. 1. As is clear to the person of ordinary skill in the art, FIG. 4 clearly shows that slit 135a is as narrow as slit 135; and FIG. 3 clearly shows that slit 135 is narrower than the outside diameter of guidewire 160. FIG. 4 also clearly shows that the slit 135a is straight throughout the length of the adapter.

As taught in Horzewski (incorporated herein by reference in the last paragraph of this specification), at Column 3, lines 31-36, and with reference to FIG. 1 of Horzewski, radiopaque marker means is provided in the form of radiopaque bands (27 and 28) which are secured to the tubular member within the balloon near the distal and proximal extremities of the balloon. Suitable material such as gold, tungsten or platinum may be utilized for the bands.

At Column 2, lines 30-68, Horzewski teaches that, in order to achieve the desirable stiffness for the shaft, the tubular member may be formed so that it has varying degrees of stiffness with decreasing stiffness towards the distal extremity of the same. The tubular member can be formed of a suitable material such as a polyolefin of various densities. The formation of the tubular member having different outside diameters and/or materials having different stiffnesses can be readily accomplished by extruding the two portions in separate extrusions using the desired ratio of high density and low density materials.

Further, Horzewski teaches at Column 4, lines 16-34 (and with reference to FIG. 7 of Horzewski), that if it is desired to provide additional stiffness in the proximal extremity of the tubular member, a mandrel (34) can be inserted into the portion of the lumen (16) proximal of the plug (31) to serve as a stiffener. The mandrel can have suitable dimensions, as for example, a portion having a continuous diameter of approximately 0.020 inches for approximately 98 centimeters of its length from its proximal extremity, with a distal portion having a continuous taper of 10 centimeters tapering down to a final dimension of approximately 0.012 inches. The mandrel can be utilized for properly positioning a plug in the first lumen and can be left in place to serve as the stiffener. The mandrel can be formed of a suitable material such as stainless steel. If the mandrel is to be used as a stiffener it is preferrable to flatten approximately 1 centimeter of the distal top of the mandrel and locate this portion within the plug to secure the mandrel in place.

With reference to FIGS. 5-9, the delivery of balloon dilation catheter 100 will be described.

Figure 5:
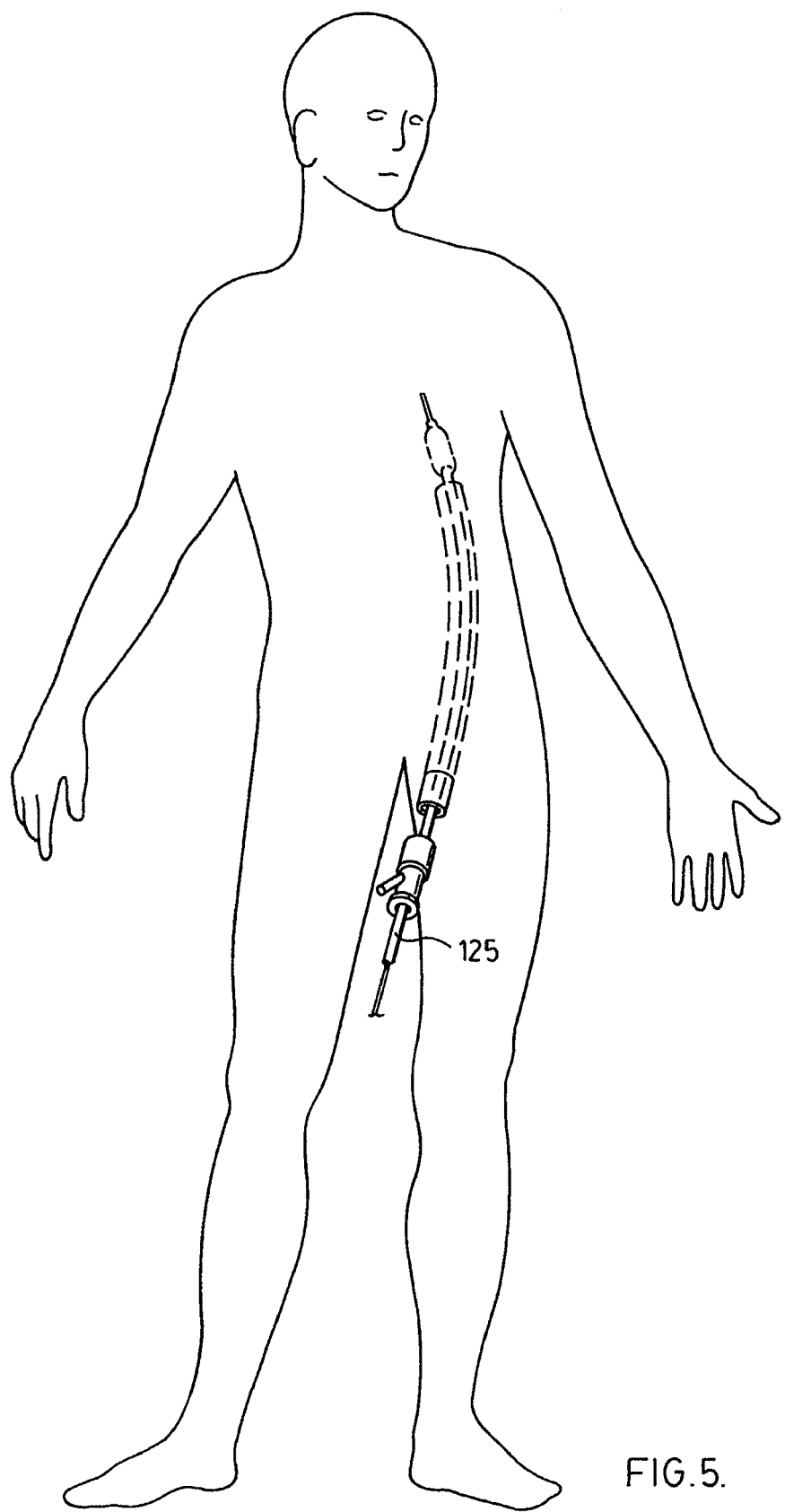

As is known in the art, catheterization is normally performed to alleviate a lesion in an artery. This is shown schematically in FIGS. 6-9 wherein a lesion in the form of a blockage 15 obstructs an artery 20. In certain cases, it is desirable to deploy a stent at the site of the lesion to maintain the patency of artery 20 at the site of blockage 15. As shown in FIG. 5, catheterization is performed through an incision in the groin area of the patient.

Thus, with reference to FIGS. 6 and 7, a guide catheter 25 is initially delivered into artery 20 to a region proximal of blockage 15. The proximal end of guide catheter 25 remains outside the patient.

Balloon dilation catheter 100 (FIG. 1) has mounted on balloon 115 thereof a stent 30. Further, guidewire 160 in second lumen 150 such that it emanates from opening 130 and from distal end 110 of balloon dilation catheter 100. Preferably, this is achieved in a conventional manner by feeding guidewire 160 into second lumen 150 at distal end 110 of balloon dilation catheter 100 until the proximal end of guidewire 160 emanates from opening 130.

At this point, balloon dilation catheter 100 is inserted into guide catheter 25 and guidewire 160 is navigated through artery 20 to a point distally of blockage 15 (FIG. 7).

Alternatively, it is possible to advance guidewire 160 to a point distally of blockage 15, after which the distal end of second lumen 150 of balloon dilation catheter 100 is passed onto the proximal end of guidewire 160. If it becomes difficult to advance guidewire 160 across blockage 15 using this technique, it is possible to advance balloon dilation catheter over the proximal end of guidewire 160 until that end exits opening 130 and the system may used in the "over-the-wire" approach described herein.

In FIG. 8, there is illustrated removal of guidewire 160 while leaving balloon dilation catheter 100 in position at point proximal to blockage 15. This is an advantageous feature of the present balloon dilation catheter which is not possible with the balloon dilation catheter taught in Horzewski. Thus, guidewire 160 may simply be replaced with another guidewire by removing the original guidewire from proximal end 105 of balloon dilation catheter 100 and simply inserting a replacement guidewire (not shown) into the proximal end 105 of balloon dilation catheter 100 and through tubular member 125. Thereafter, the replacement guidewire may be navigated so that it emanates from distal end 110 of balloon dilation catheter 100. The replacement guidewire is navigated to a point distal of blockage 15.

Balloon dilation catheter 100 is then navigated over the replacement guidewire such that stent 30 is in proper position with respect to blockage 15 (FIG. 8). Once the guidewire and balloon dilation catheter 100 are in the correct position, fluid is injected into first lumen 150 thereby expanding balloon 115 and stent 30 mounted thereon. Deployment of a stent in this manner is conventional and within the purview of a person skilled in the art.

In FIGS. 10 and 11, there is illustrated rapid exchange of balloon dilation catheter 100 while leaving guidewire 160 in place. In this case, for clarity, stent 30 is not shown on balloon 115. One of the features of the present balloon dilation catheter which distinguishes it from that in Horzewski is that guidewire 160 emanates from a proximal portion of balloon dilation catheter 100 which is always outside the body of the patient. This provides the practitioner with the "over-the-wire" approach described above. Thus, either opening 130 is located outside the body at all times during use of catheter 100 illustrated in FIG. 1 or it is necessarily emanating from the proximal end of balloon dilation catheter 100 if the modified embodiment in FIG. 4 is utilized.

When it is desired to exchange balloon dilation catheter 100, the balloon dilation catheter is withdrawn from artery 20 while leaving guidewire 160 in place. As balloon dilation catheter 100 is withdrawn from the body of the patient, it may be readily separated from guidewire 160 via slit 135 along virtually the entire length of tubular member 125—this is one of the principal advantages of the present balloon dilation catheter which, to the knowledge of the present inventors, has not been achieved with a prior balloon dilation catheter. Once distal end 110 of balloon dilation catheter 100 is withdrawn from the body, balloon 115 may be exchanged from guidewire 160 in a conventional manner.

A replacement balloon dilation catheter may then be fed over guidewire 100 and navigated into artery 20 in the area of blockage 15.

With reference to FIG. 12, there is illustrated yet a further alternate embodiment to the present balloon dilation catheter. In this case, a slit 135*b* is provided in balloon 115*b* such that slit 135 is in communication with slit 135*b* on balloon 115*b*. This modification of balloon catheter 100 is particularly advantageous when the catheter is being used in an angioplasty application (i.e., without a stent mounted on balloon 115) as a pre-dilation balloon catheter allowing for enhanced rapid exchange features by facilitating withdrawal of guidewire 160 in a rapid exchange manner along virtually the entire length of tubular member 125 and balloon 115*b* via the combination of slits 135 and 135*b*. This feature is generally advantageous since it facilitates withdrawal of the balloon dilation catheter from the patient.

With reference to FIG. 13, there is illustrate a preferred modification to tubular member 125 of balloon catheter 100. Specifically, a third lumen 180 is provided along substantially the entire length of tubular member 125. Disposed within third lumen 180 is a stiffening member 185 which serves to improve the "torqueability" of balloon dilation catheter. Unlike, the approach in Horzewski described above wherein a single lumen does double duty for receiving: (i) a stiffening member along most of the length of the catheter and (ii) the guidewire along a minor portion of its length, the approach shown in FIG. 13 is a significant improvement over Horzewski since it maximizes both the distance over which rapid exchange may be effected and the distance over which stiffening may be conferred to the tubular member.

While this invention has been described with reference to illustrative embodiments, this description is not intended to be construed in a limiting sense. For example, while the illustrated embodiments depict use of the present balloon dilation catheter in delivery of a stent, those of skill in the art will immediately appreciate that the present balloon dilation catheter may be used in percutaneous transluminal coronary angioplasty techniques. Various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A balloon catheter comprising:
   a tubular member having a proximal end and a distal end;
      an inflatable balloon disposed at the distal end of the tubular member; a stent mounted on the inflatable balloon;
   a first lumen disposed in the tubular member and in communication with an interior of the inflatable balloon;
   a second lumen disposed in the tubular member for receiving a guidewire substantially along its entire length, the second lumen having a first opening at the proximal end of the tubular member and a second opening at the distal end of the tubular member;
   a first slit disposed longitudinally from the first opening along the tubular member to permit separation of the guidewire with respect to the second lumen; wherein the inflatable balloon comprises a second slit in substantial alignment with the first slit;
   an adapter disposed at the proximal end of said tubular member; and
   an adapter slit disposed in said adapter to permit separation of the guidewire from the adapter, said adapter slit being narrower than an outside diameter of the guidewire, said adapter slit being straight from a proximal end of the catheter to a proximal end of the adapter.

2. The balloon catheter defined in claim 1, wherein the first slit extends from the first opening to an area on the tubular member which is proximal to the inflatable balloon.

3. The balloon catheter defined in claim 1, wherein the slit extends from the first opening to the second opening.

4. The balloon catheter defined in claim 1, further comprising a third lumen for receiving a stiffening member.

5. The balloon dilation catheter defined in claim 4, further comprising the stiffening member disposed in the third lumen.

6. The balloon catheter defined in claim 5, wherein the stiffening member comprises a metal wire.

7. The balloon catheter defined in claim 1, wherein the first lumen and the second lumen each comprise a passageway having a substantially circular cross-section disposed in a substantially solid tubular member.

8. The balloon catheter defined in claim 1, further comprising at least one radioopaque marker disposed on the tubular member.

9. The balloon catheter defined in claim 1, wherein the tubular member is constructed from plastic material having various density to provide a decreasing stiffness from the proximal end to the distal end.

10. The balloon catheter defined in claim 1, wherein said adapter slit consists of a straight slit throughout the length of said adapter.

11. A balloon catheter comprising:
   a tube having a proximal end and a distal end;
   a balloon disposed at the distal end of the tube;
   a stent mounted on the balloon;
   a first lumen disposed in the tube and in communication with an interior of the balloon;
   a second lumen disposed in the tube configured for receiving a guidewire along the length of the second lumen, the second lumen having a first opening at the proximal end of the tube and a second opening at the distal end of the tube;
   a first slit disposed longitudinally from the first opening along the tube member to permit separation of the guidewire from the second lumen through the first slit; wherein the balloon has a second slit in substantial alignment with the first slit;
   an adapter connected to the proximal end of said tube; and
   an adapter slit disposed in said adapter to permit separation of the guidewire from the adapter through the adapter slit, said adapter comprising a straight slit throughout the entire length of said adapter from a proximal end of the catheter to a proximal end of the adapter.

12. The balloon catheter defined in claim 11, wherein said adapter slit is narrower than an outside diameter of the guidewire.

13. The balloon catheter defined in claim 12, wherein said adapter slit is as narrower as said first slit.

14. The balloon catheter defined in claim 12, wherein, wherein the tube is constructed from plastic material having various densities to provide a decreasing stiffness from the proximal end to the distal end.

15. The balloon catheter defined in claim 12, wherein said first slit extends from the first opening along the length of the tube to a location proximal the balloon.

16. The balloon catheter defined in claim 12, wherein said adapter comprises:
    a guidewire branch; and
    an inflation branch angled with respect to said guidewire branch.

17. The balloon catheter defined in claim 12, wherein said adapter has at least two sections with different diameters.

18. A stent-mounted balloon catheter comprising:
    a tube having a proximal end and a distal end;
    a balloon disposed at the distal end of the tube;
    a stent mounted on the balloon;
    a first lumen disposed in the tube and in communication with an interior of the balloon;
    a second lumen disposed in the tube configured for receiving a guidewire along the length of the second lumen, the second lumen having a first opening at the proximal end of the tube and a second opening at the distal end of the tube;
    a first slit disposed longitudinally from the first opening along the tube member to permit separation of the guidewire from the second lumen through the first slit;
    wherein the balloon has a second slit in substantial alignment with the first slit;
    an adapter connected to the proximal end of said tube; an adapter slit disposed in said adapter to permit separation of the guidewire from the adapter, said adapter slit being narrower than an outside diameter of the guidewire, said adapter slit comprising a straight slit; and
    a third lumen disposed in said tube between the first and second lumens, a non-guidewire stiffening member being disposed in at least a portion of said third lumen.

19. A balloon catheter comprising:
    a tubular member having a proximal end and a distal end;
    an inflatable balloon disposed at the distal end of the tubular member; a stent mounted on the inflatable balloon;
    a first lumen disposed in the tubular member and in communication with an interior of the inflatable balloon;
    a second lumen disposed in the tubular member for receiving a guidewire along at least a portion of its length, the second lumen having a first opening at the proximal end of the tubular member and a second opening at the distal end of the tubular member;
    a first slit disposed longitudinally from the first opening along the tube member to permit separation of the guidewire from the second lumen through the first slit; wherein the inflatable balloon has a second slit in substantial alignment with the first slit;
    an adapter disposed at the proximal end of said tubular member; and
    an adapter slit disposed in said adapter to permit separation of the guidewire from the adapter, said adapter slit being narrower than an outside diameter of the guidewire throughout the entire length of the adapter, said adapter slit comprising a straight slit from a proximal end of the catheter to a proximal end of the adapter.

20. The balloon catheter defined in claim 19, wherein said adapter slit is as narrower as said first slit.

21. The balloon catheter defined in claim 19, wherein said first slit is narrower than an outside diameter of the guidewire.

\* \* \* \* \*